(12) United States Patent
Monteiro Carneiro

(10) Patent No.: US 8,273,121 B2
(45) Date of Patent: Sep. 25, 2012

(54) PROCESS OF USE OF A DEVICE FOR CORNEA TRANSPLANTATION

(76) Inventor: Adriano Biondi Monteiro Carneiro, Sao Jose Dos Campos (BR)

(*) Notice: Subject to any disclaimer, the term of this patent is extended or adjusted under 35 U.S.C. 154(b) by 231 days.

(21) Appl. No.: 12/602,185

(22) PCT Filed: May 30, 2008

(86) PCT No.: PCT/BR2008/000156
§ 371 (c)(1),
(2), (4) Date: Nov. 30, 2009

(87) PCT Pub. No.: WO2008/144870
PCT Pub. Date: Dec. 4, 2008

(65) Prior Publication Data
US 2010/0198197 A1 Aug. 5, 2010

(30) Foreign Application Priority Data

May 30, 2007 (BR) .................................. 0702038
May 28, 2008 (BR) ............................. C10702038-4

(51) Int. Cl.
*A61F 2/14* (2006.01)

(52) U.S. Cl. ...................... 623/5.12; 623/5.14; 606/213
(58) Field of Classification Search .......... 623/5.11–5.16
See application file for complete search history.

(56) References Cited

U.S. PATENT DOCUMENTS
6,508,837 B1 * 1/2003 Silvestrini .................... 623/5.11
* cited by examiner

*Primary Examiner* — Thomas J Sweet
*Assistant Examiner* — Joshua Levine
(74) *Attorney, Agent, or Firm* — Galbreath Law Offices, P.C.; John A. Galbreath

(57) ABSTRACT

The invention is a surgical instrument (1) used in ophthalmology, which allows a penetrating or lamellar cornea transplant without the use of suture. It comprises a set of arc segments interconnected by a small diameter polypropylene wire (2), which goes through the internal body structure of each segment. The first arc segment (3), also called the segment guide, is an arc of 160-330 degrees with a circular cross-section and a rounded edge. The second arc segment (4), also called the main segment, is an arc of 270-360 degrees, and has a horizontal or oblique cross-section tangential to the surface of the cornea, or a circular cross-section. The third arc segment (5), also called the secondary segment, has a thickness or cross-section greater than that of the main segment.

2 Claims, 1 Drawing Sheet

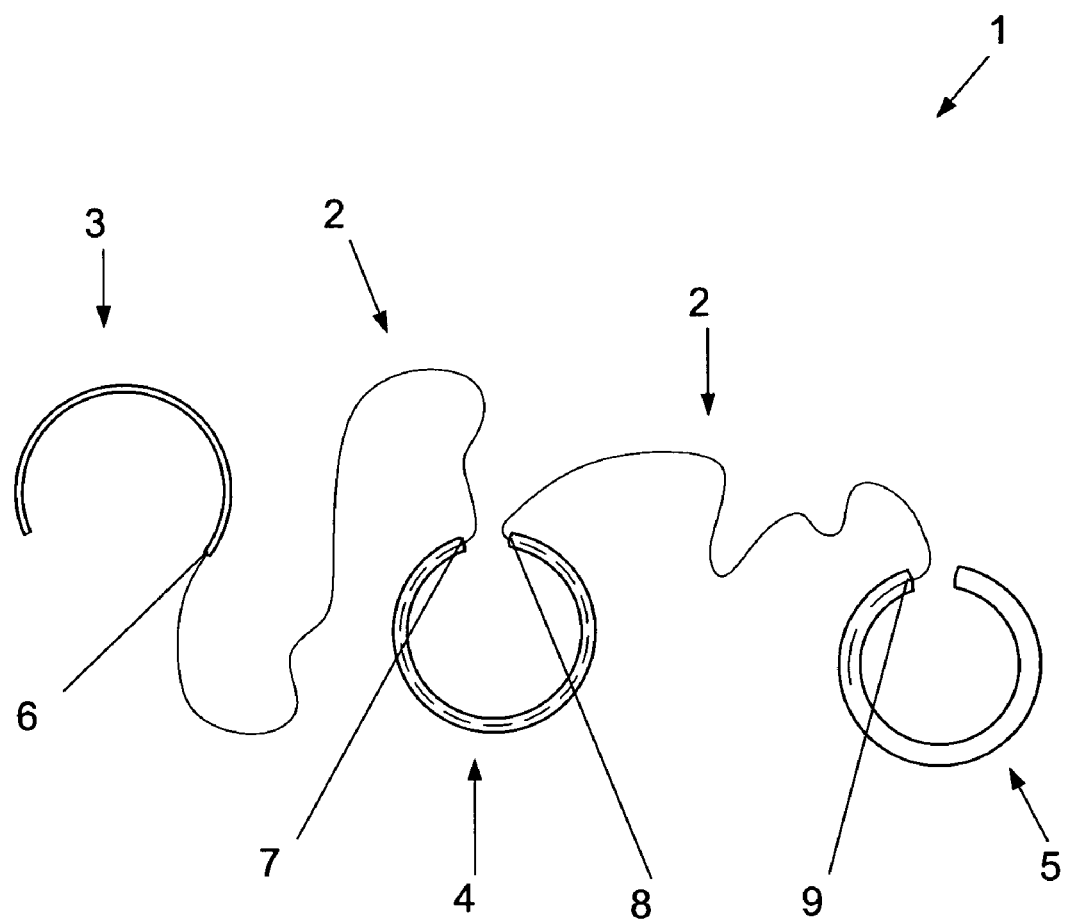

PROCESS OF USE OF A DEVICE FOR CORNEA TRANSPLANTATION

BACKGROUND OF THE INVENTION

1. Field of the Invention

The invention is a surgical device used in the field of ophthalmology, which allows penetrating or lamellar cornea transplant surgery to be performed without the use of suture.

2. Description of Related Art

Cornea transplantation is a complex procedure, which is currently done by joining the central portion of a cornea from a donor with the peripheral portion of the cornea of the recipient. The cornea transplantation process is very important for the resolution of many diseases that affect significant parts of the world population, including the loss of transparency of the cornea, or the modification of the cornea's curvature which induces abnormalities in the projection of light to the retina and consequent visual limitation.

In cornea transplantation, the setting, capping, and cooptation between the donor tissue and recipient tissue is crucial to achieving a satisfactory optical and functional outcome after surgery. Currently, the procedure is performed through a mechanical trephination, with a button of cornea tissue being excised from the cornea recipient. A button of cornea tissue is also excised from the cornea donor by trephination. The button of cornea tissue has a circular format, and the diameter can vary depending on the purpose of the surgery. After adequate preparation of the donor tissue, which can be done in an artificial anterior chamber to facilitate handling, the donated cornea is then placed in the same position where the cornea was trephinated from the recipient patient. After positioning and smoothing the donor cornea, sutures are made with yarn of a small size, usually Nylon 10-0, separated in the vast majority of cases, in order to obtain the best possible junction between the recipient and donor tissue.

For that to occur, it is essential that a proper trephination of both corneas be performed, particularly when the trephinations are made by different types of mechanical trephination. There can be no openings between the donor and recipient tissue, in order to prevent the leakage of aqueous humor which is present in the anterior chamber of the eye. In order to correctly seal, the suture points must be tight. However, this induces large abnormalities in the format of previous surface of the cornea, which eventually causes significant astigmatism.

With the advent of the incorporation of femtosecond laser technology in medical practice, particularly in ophthalmology, new opportunities for preparation of cuts in the cornea are being proposed. The possibility currently exists of conducting the trephination in both the cornea recipient and the cornea donor in a more complex way, with precise incisions in the vertical and horizontal planes, and with strong tangential cuts to the surface of the cornea. The depths of these cuts can be established and the planned in sync between the tissue donor and recipient, increasing the precision of the procedure.

DISADVANTAGES OF THE CURRENT STATE OF THE ART

Despite the significant number of cornea transplants, there are still some drawbacks to the current surgical procedure. The sutures in the cornea transplant must be carried out very carefully, so that a perfectly aligned plane is obtained in front of the corneal surface, and so that the corneal surface is regular and even. However, even if the suture is perfect, whether a separate or continuous suture, it is technically impossible to maintain reproducibility and predictability from one suture points to another, even if all the sutures are performed by a single surgeon. This variability results in post-operative corneal astigmatism, which often occurs in ophthalmology surgery, and which is the main limiter of good visual quality for patients that undergo cornea transplantation.

The advent of femtosecond laser technology opened new perspectives and new ways for performing cornea intersectional surgery and lamellar or penetrating transplants of corneas with high precision, but there are still great disadvantages in the applicability and costs of these procedures.

Although the cuts needed to prepare for cornea transplants are increasingly precise and predictable with a femtosecond laser, there is still the need for continuous or separate suturing in order to properly seal the anterior chamber of the eye and obtain the proper cooptation between the donor and recipient tissues, and this virtually negates the advantages in precision and procedure optimization offered by a femtosecond laser. Currently, other surgical procedures are often required after the cornea transplantation to bring about a surface with regular and balanced sphericity to provide good vision to the patient. For example, one can use an excimer laser to settle the area after the transplant.

The femtosecond laser has been used to make selective cuts of donor and recipient corneas to produce thin corneal sections with defined diameters, and this has provided an improvement in the results of lamellar cornea transplants, such as endothelial transplants whose technique is still evolving. Other options such as the use of an intra-stomal ring and, more recently, therapy using the cross linking of collagen have gained popularity, though these are still missing randomized clinical trials to test their effect in the long term.

SUMMARY OF THE INVENTION

Thinking about possible improvements to the surgical procedures of cornea transplants, in order to have a better, more reliable, and more predictable result, has led the inventor to develop, design and develop the device for cornea transplantation without suture disclosed herein. It is an apparatus for making implants in the cornea, which dispenses with the need for manual suturing, whether continuous or separate.

The device consists of a series of segments of semi-rigid arcs, which are interconnected through a wire that pass through the internal body structure of each arc segment. The wire size is small enough to go through the rigid structure of the arc segments, without changing their shape and resistance.

The invention aims to provide an ophthalmic device which can be implanted in the stroma of the cornea, which is extremely efficient, and which is properly developed and devised to allow surgeons to have reliability, safety and low cost, and to perform their duties with efficiency and simplicity. The invention demonstrates unmatched versatility and practicality, and incorporates unique features.

The invention is built with durable materials, is inert with respect to the corneal tissue, and has robust characteristics. It offers ophthalmic surgeons quality, economy, security, reliability and predictability of the outcome of a cornea transplant.

The figures shown and described herein express the best or preferred way of constructing and using the device.

These figures are purely illustrative and may vary without departing from the spirit of the invention.

BRIEF DESCRIPTION OF THE DRAWINGS

FIG. 1 shows the device for cornea transplants without suture, and illustrates the first arc segment (segment guide), the second arc segment (main segment), and the third arc segment, which are united by a thread made of a polypropylene such as Prolene®.

DETAILED DESCRIPTION OF THE INVENTION

As seen in FIG. 1, the inventive device for cornea transplantation without suture comprises an apparatus consisting of a series of arc segments of interconnected through a wire, which goes through the internal body structure of each arc segment. The first arc segment 3, also referred to herein as the "segment guide", is an arc segment which is preferably made of polymethylmethacrylate (PMMA), and which can vary from an arc of 160 degrees to an arc of 330 degrees. First arc segment 3 has a circular cross-section and a rounded edge, to help it slide inside a tunnel-like opening made previously by a femtosecond laser in both the donor cornea and the recipient cornea, and progress along that opening. First arc segment 3 is a circular segment, and its diameter can range from 5 to 11 mm depending on the purpose of the transplantation and the surgeon's plans.

The first arc segment 3 or segment guide is connected at an end 6 thereof to a second arc segment 4 by a polypropylene wire 2. Second arc segment 4, also referred to herein as the "main segment", is the primary means of achieving cooptation between the donor cornea and the recipient cornea, is built preferably of PMMA, and can vary from an arc of 270 degrees to an arc of 360 degrees. Second arc segment 4 has a thickness or cross-section that is horizontal or oblique, tangential to the surface of the cornea, or a circular cross section. Second arc segment 4 or main segment has an initial end 7 and a far end 8 attached to polypropylene wire 2, preferably the "10-0" variety, which goes through and along the internal body structure of second arc segment 4. The function of polypropylene wire 2 is to bring the main segment inside the tunnel made in the donor cornea and the recipient cornea by the femtosecond laser, after the passage of the first arc segment 3 or segment guide which has a small size and a rounded edge to facilitate their integration and advancement.

Polypropylene wire 2 emerges from the second arc segment (4) or main segment, and may connect to an initial end 9 of a third arc segment 5, also referred to herein as the "secondary segment". The third arc segment's diameter will be the same as that of the main segment and also the segment guide. However, the thickness or cross-section of the third arc segment 5 may be 50% higher compared with that of the second arc segment 4 or main segment, to provide greater firmness and cooptation between the donor cornea and the recipient cornea, if the surgeon feels that the main segment was not thick enough (i.e., of large enough cross-section) to adequately join the donor cornea and the recipient cornea. Thus, third arc segment 5 may or may not be necessary.

After the insertion of the second arc segment 4 or main segment in the tunnel made by the femtosecond laser, the main segment can be separated from the other segments by cutting polypropylene wire 2, so that only one segment remains in the stroma of the cornea. The depth of the cut by the femtosecond laser can be managed by the surgeon, to provide the same depth and good alignment between the donor cornea and recipient cornea. The ends of the polypropylene wire 2 may be knotted by the surgeon to increase the stability between the ends of the rigid segment now implanted in the cornea. This segment will remain in the cornea until natural healing occurs between the donor cornea and the recipient cornea.

It can be seen from the foregoing that the inventive device for cornea transplantation without suture allows a penetrating or lamellar cornea transplant assisted by a femtosecond laser, without using a suture. The invention has many technical advantages over the conventional models currently on the market, as well as construction and functional characteristics that are completely different from the current state of the art.

The invention claimed is:

1. A device for cornea transplantation without suture, comprising:
   a series of arc segments interconnected by a flexible wire made from material which is inert to the cornea, said flexible wire disposed in an internal body structure of each said arc segment, and wherein said series of arc segments comprise:
   a first arc segment measuring between 160 and 330 degrees, said first arc segment having a circular cross-section and a rounded edge;
   a second arc segment, said second arc segment being a means for achieving cooptation between a donor cornea and a recipient cornea in said cornea transplantation, and said second arc segment measuring between 270 and 360 degrees; and
   a third arc segment, said third arc segment having a cross-section which is greater than the cross-section of said second arc segment.

2. The device for cornea transplantation without suture of claim 1, wherein said first arc segment has an end thereof which is attached to said flexible wire, said flexible wire being set in an initial end of said second arc segment and passing lengthwise through said second arc segment, and said flexible wire being fixed at a far end of said second arc segment and also being fixed at an initial end of said third arc segment.

* * * * *